United States Patent [19]

Hesse

[11] Patent Number: Plant 6,392

[45] Date of Patent: Nov. 15, 1988

[54] KALANCHOE PLANT NAMED LA PAZ

[75] Inventor: Peter S. Hesse, Bradenton, Fla.

[73] Assignee: Ball Pan Am Plant Co., Parrish, Fla.

[21] Appl. No.: 6,134

[22] Filed: Jan. 23, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named La Paz, characterized by its pink and light orange bicolored flower, compact and free branching habit, early flowering, very floriferous habit, and by its adaptability to production in 10 to 15 cm pots.

1 Drawing Sheet

1

The present invention relates to a new and distinct cultivar of Kalanchoe plant, botanically known as Kalanchoe, and referred to by the cultivar name La Paz.

The new cultivar was referred to during the breeding and selection process by the designation K82-404H-P, and is a product of a planned breeding program. The basic objective of the breeding program was to create a new Kalanchoe cultivar having compact habit, soft pink flower color, free branching, good keeping quality, and early flowering response.

La Paz was originated from a cross made in a controlled breeding program in Parrish, Fla. The female, or seed parent was a cultivar designated Firefly (disclosed in U.S. Plant Pat. No. 4,728). The male, or pollen parent was the cultivar Sensation (disclosed in U.S. Plant Pat. No. 4,727).

La Paz was discovered and selected by me as a flowering plant within the progeny of the stated cross in a controlled environment in Parrish, Fla. Asexual reproduction of the new cultivar by stem cuttings, as performed by me at Parrish, Fla., has demonstrated that the combination of characteristics as herein disclosed for the new cultivar are firmly fixed and are retained through successive generations of asexual reproduction.

La Paz has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of La Paz, which in combination distinguish this Kalanchoe as a new and distinct cultivar:

1. General tonality of flower color at 3 feet is pink. Closer observation reveals a unique mixture of pink and orange flowers.
2. Compact habit and average growth rate.
3. Freely branching, with shoots formed at every node.
4. Suitable for production in 10–15 cm pots, and flowering in 12–15 weeks using photoperiodic control.
5. Very floriferous, with numerous flowers formed at every node.
6. Responds to B-9 applications to control height.
7. Medium sized leaves which are very thick and persistent.

2

The new cultivar is most similar to Citation, disclosed in U.S. Plant Pat. No. 5,533. Chart A attached hereto compares certain characteristics of both La Paz and Citation. La Paz is principally distinguished from Citation by its larger, pink and soft orange bicolored flowers, earlier flowering response, more vigorous growth habit, and lighter foliage color.

The accompanying photographic drawing shows a typical specimen plant of the new cultivar. The photograph is in black and white, with certain flowers being colored to accurately depict true flower color. The bicolor feature will be readily noted.

In the following description, color references are made to The Royal Horticultural Society Colour Chart (R.H.S.), except where general colors of ordinary significance are referred to. Color values are taken under fluorescent light conditions in September in Parrish, Fla.

Botanical classification: Kalanchoe, cv. La Paz.

Parentage:

*Male parent.*—Sensation.

*Female parent.*—Firefly.

Propagation: The new cultivar holds its distinguishing characteristics through successive propagations by leaf cuttings and by division of shoots.

(A) *Type cutting.*—Shoot tip.

(B) *Time to root.*—Summer: 10–14 days at 21° C.

(C) *Rooting habit.*—Fibrous, many very fine roots.

Plant description:

(A) *Form.*—Upright, short compact growth. Scheduling practices can produce small plants in 10 cm pots or large plants in 15 cm pots.

(B) *Habit of growth.*—Average rate for this type of plant. Shoots are formed at every node.

(C) *Foliage description.*—Leaves simple, opposite, ovate with unevenly crenate margins. (1) Size: up to 13 cm long. Up to 9 cm wide. (2) Shape: Ovate. (3) Texture: Smooth, waxy and succulent. (4) Margin: Unevenly crenate. (5) Color: Young and mature foliage, top side 147B, under side 147C.

Flowering description:

(A) *Flowering habit.*—Compound dichasial cyme on strong peduncles. Peduncle length depends upon growing conditions and B-9 application. Pedicels up to 5 mm long.

(B) *Natural flowering season.*—Fall. Flowering time under controlled day length at 75°–85° F. in summer is 12–14 weeks; in Winter at 62°–70° F., 14–16 weeks. Flowering time depends on temperature light intensity and other growing conditions.

(C) *Flower buds.*—Oblong, developing to tubular as petals mature. Sheathed with four green sepals. Corolla at maturity about 10–13 mm long. (1) Size: 10–13 mm long. (2) Shape: Oblong. (3) Rate of opening: Normal.

(D) *Flowers borne.*—Compound dichasial cyme on strong peduncles. Peduncle length depends on growing conditions and B-9 applications. Pedicles up to 5 mm long.

(E) *Quantity of flowers.*—Corolla funnel shaped, petal apex abruptly acuminate.

(F) *Petals.*—(1) Shape: Ovate with apex acuminate. (2) Color: Top side when opening, primarily 38A and 63B, faded to 38B and 63C; under side, 63D. All of the top side colors noted appear in the photographic drawing, and the unique bicolor characteristic is depicted. Counting mature and immature colors visible at the same time, the four separate colors (and tones thereof) provide a distinct appearance. (3) Number and size of petals: Four (4), petals 7 mm in diameter, total flower diameter 18 mm.

(G) *Reproductive organs.*—(1) Stamens: Eight (8) in number. (a) Anther shape: Flat, Elliptical. (b) Filament color: Yellow. (c) Pollen color: Yellow. (2) Pistels (a) Stigma shape: Flat, crystalline. (b) Style color: Greenish white. (c) Ovaries: 4-celled, 7 mm long, green.

Disease resistance: No known Kalanchoe diseases observed to date.

General Observations: La Paz is principally characterized by its pale to medium pink and soft orange flower petals, a very distinctive show of color.

CHART A

La Paz vs. Citation
Summer Conditions

| | La Paz | Citation |
|---|---|---|
| Mature flower color | Bi-Color 63B and 38A | 52 A |
| Flowering plant height | 23 cm | 20 cm |
| Weeks to flower | 12 | 14 |
| Mature leaf width | 7.5 cm | 8 cm |
| Mature leaf length | 13 cm | 14 cm |
| Diameter of Flower | 18 mm | 15 mm |
| Leaf color | 147 B | 147 A |

The plants of La Paz and Citation which were used in this comparison were grown together on the same bench in a greenhouse in Parrish, Fla. The color readings were taken under fluorescent light at 3:00 pm on Sept. 17, 1986.

I claim:

1. A new and distinct cultivar of Kalanchoe plant named La Paz, as described and illustrated, and particularly characterized by its pink and light orange bicolored flower, compact and free branching habit, early flowering, very floriferous habit, and by its adaptability to production in 10 to 15 cm pots.

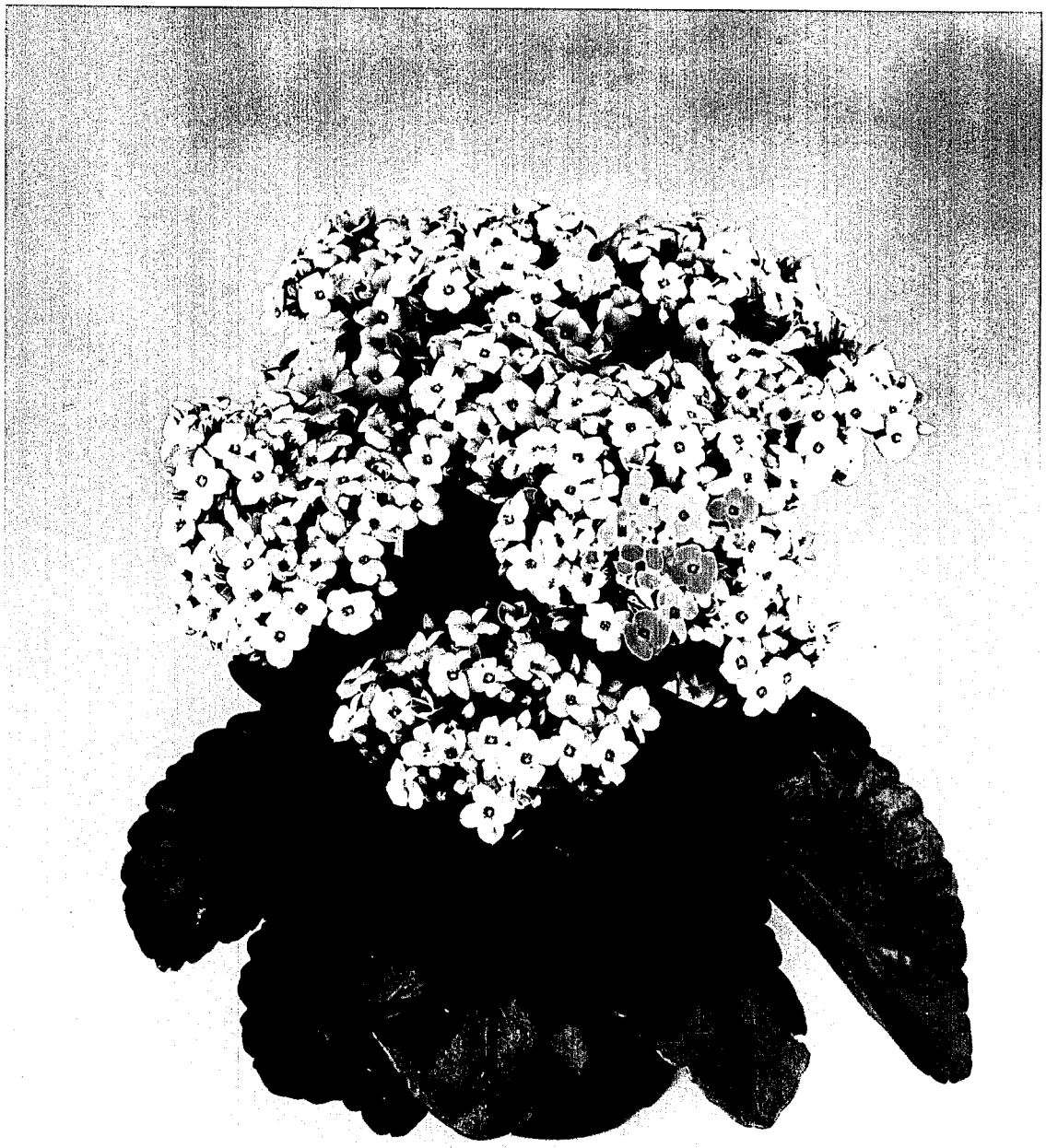

* * * * *